United States Patent [19]

Viola

[11] Patent Number: 5,439,155
[45] Date of Patent: Aug. 8, 1995

[54] CARTRIDGE FOR SURGICAL FASTENER APPLYING APPARATUS

[75] Inventor: Frank J. Viola, Sandy Hook, Conn.
[73] Assignee: United States Surgical Corporation, Norwalk, Conn.
[21] Appl. No.: 350,583
[22] Filed: Dec. 6, 1994

Related U.S. Application Data

[63] Continuation of Ser. No. 133,697, Oct. 7, 1993, abandoned.
[51] Int. Cl.$^6$ ............................................. A61B 17/068
[52] U.S. Cl. ..................................... 227/176; 227/19; 227/178
[58] Field of Search ............... 227/175, 176, 177, 178, 227/181, 19

[56] References Cited

U.S. PATENT DOCUMENTS

| | | |
|---|---|---|
| 3,080,564 | 3/1963 | Strekopitov et al. |
| 3,252,643 | 5/1966 | Strekopytov et al. |
| 3,269,630 | 8/1966 | Fleischer . |
| 3,275,211 | 9/1966 | Hirsch et al. . |
| 3,494,533 | 2/1970 | Green et al. . |
| 3,589,589 | 6/1971 | Nikowovsky . |
| 3,692,224 | 9/1972 | Astafiev et al. . |
| 3,795,034 | 3/1974 | Strekopytov et al. . |
| 4,108,306 | 8/1978 | Samuels et al. . |
| 4,256,251 | 3/1981 | Moshofsky . |
| 4,305,539 | 12/1981 | Korolkov et al. . |
| 4,349,028 | 9/1982 | Green . |
| 4,354,628 | 10/1982 | Green . |
| 4,383,634 | 5/1983 | Green . |
| 4,402,445 | 9/1983 | Green . |
| 4,415,112 | 11/1983 | Green . |
| 4,506,670 | 3/1985 | Crossley . |
| 4,506,671 | 3/1985 | Green . |
| 4,508,253 | 4/1985 | Green . |
| 4,513,746 | 4/1985 | Aranyi et al. . |
| 4,522,327 | 6/1985 | Korthoff et al. . |
| 4,530,453 | 7/1985 | Green . |
| 4,566,620 | 1/1986 | Green et al. . |
| 4,568,009 | 2/1986 | Green . |
| 4,573,622 | 3/1986 | Green et al. . |
| 4,576,167 | 3/1986 | Noiles . |
| 4,580,712 | 4/1986 | Green . |
| 4,585,153 | 4/1986 | Failla et al. . |
| 4,591,085 | 5/1986 | DiGiovanni . |
| 4,605,004 | 8/1986 | DiGiovanni et al. . |
| 4,606,344 | 8/1986 | DiGiovanni . |
| 4,606,345 | 8/1986 | Dorband et al. . |
| 4,607,636 | 8/1986 | Kula et al. . |
| 4,632,290 | 12/1986 | Green et al. . |
| 4,646,745 | 3/1987 | Noiles . |
| 4,665,916 | 5/1987 | Green . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,869,414 | 9/1989 | Green et al. . |
| 4,881,544 | 11/1989 | Green et al. . |
| 4,881,545 | 11/1989 | Isaacs et al. . |
| 4,915,100 | 4/1990 | Green . |
| 4,978,049 | 12/1990 | Green . |
| 5,071,052 | 12/1991 | Rodak et al. . |
| 5,100,042 | 3/1992 | Gravener et al. . |
| 5,137,198 | 8/1992 | Nobis et al. . |

FOREIGN PATENT DOCUMENTS

| | | |
|---|---|---|
| 0067743 | 12/1982 | European Pat. Off. . |
| 0136950 | 4/1985 | European Pat. Off. . |
| 0220029 | 4/1987 | European Pat. Off. . |
| 0246870 | 11/1987 | European Pat. Off. . |
| 1835500 | 4/1961 | Germany . |

OTHER PUBLICATIONS

Proximate RL Plus Reloadable Linear Stapler, Ethicon, Inc., 1990.
Information Booklet for Auto Suture ® Premium Poly CS TM -57 Disposable Surgical Stapler, United States Surgical Corporation, 1986.
Information Booklet for Auto Suture ® Poly CS TM -57 Disposable Surgical Stapler, United States Surgical Corporation, Jul. 1988.
Information Booklet for Auto Suture ® Poly CS TM -57 Disposable Loading Units With Lactomer ® Absorbable Copolymer Stapels, United States Surgical Corporation, Jul. 1988.

Primary Examiner—Scott A. Smith

[57] ABSTRACT

A surgical stapling or fastening instrument for applying surgical fasteners to tissue. A device for registering a removable cartridge containing the staples or fasteners into the jaw mechanism is provided, which prevents loading of an incompatible cartridge into the fastening instrument.

6 Claims, 2 Drawing Sheets

CARTRIDGE FOR SURGICAL FASTENER APPLYING APPARATUS

This is a continuation of copending application Ser. No. 08/133,697 filed on Oct. 7, 1993, now abandoned.

BACKGROUND OF THE INVENTION

1. Field of the Invention

The present invention relates to devices for applying surgical fasteners having replaceable fastener carrying cartridges, and more particularly to a means for registering the cartridge with the jaw mechanism of the instrument to prevent loading of a cartridge having incorrectly sized or positioned fasteners into the instrument.

2. Background of the Prior Art

Surgical fastening devices for simultaneously applying an array of surgical staples or other types of fasteners are known hi the art. Such devices are used for suturing body tissue such as, for example, intestinal and gastric walls with spaced parallel rows of longitudinally aligned staples. These surgical stapling devices reduce the time of wound closure in a surgical procedure.

Typically, these devices include a fastener cartridge disposed on one side of the tissue to be fastened, and an anvil assembly parallel to the fastener holder on the other side of the tissue to be fastened. The fastener cartridge is moved linearly towards the anvil assembly so that the tissue is clamped between them. The fasteners may comprise staples and are driven from the fastener cartridge so that the ends of the fasteners pass through the tissue and are formed as they make contact with the anvil assembly, thereby producing an array of formed fasteners in the tissue. Optionally, the fastening apparatus may include a knife mechanism for creating an incision between rows of fasteners. The fasteners can be made of metal, non-absorbable polymers, or bioabsorbable polymers such as polyglycolide, polylactide, and copolymers thereof. Alternately, the anvil surface may support a plurality of retainers for cooperatively engaging the fasteners after the fasteners pass through the tissue.

In common use are devices in which the fastener cartridge comprises a disposable cartridge removably mounted on a cartridge jaw. The cartridge is disposable after a single use, i.e. after the fasteners are fired. The fastener apparatus can be reloaded with a fresh cartridge. The cartridge typically comprises fasteners of a single size, with various sized cartridges available for particular applications. The size and/or arrangement of the fasteners may vary among cartridges. Some surgical apparatuses known in the art can be reusable in a subsequent surgical procedure after cleaning, sterilizing and reloading. Also known in the art are disposable surgical fastener devices, in which the entire apparatus is disposed of after a single use.

The fastening instrument includes a driving mechanism operatively associated with the actuating handle and movable to force the fasteners from the cartridge into tissue positioned between the jaw members. The amount of fasteners, their respective size, and their arrangement or orientation may be required to be preset for a particular operation, and typically, a number of cartridges may be needed to complete the surgical procedure. Depending on the operation, several different sized fasteners may be required, and a plurality of cartridges may be present during the surgery. With such instruments utilizing replaceable cartridges, it would be advantageous to ensure the interchangeability of compatible cartridges in the instrument. It would also be advantageous to provide a readily visible mechanism to achieve this objective.

The novel cartridge and jaw mechanism of the present invention, and in particular its means for registering the cartridge with the jaw mechanism of the surgical fastener applying instrument advantageously provides a means for visually and operatively preventing the loading of an incompatible cartridge onto a fastener applying instrument. A registering tab is provided on the cartridge which is accepted by a complementary notch in the cartridge jaw. The tab and notch are positioned at specific locations corresponding to specific sizes of cartridges, specific arrangements or orientations of fasteners, and/or specific quantities of fasteners. The registering tabs are also configured in such a manner so as to provide a means for grasping the cartridge to facilitate its insertion into the jaw mechanisms. The tabs may also provide a visual indication of the fasteners associated with a particular cartridge.

SUMMARY OF THE INVENTION

The present invention provides a surgical fastening apparatus for applying a plurality of surgical fasteners to body tissue which includes means for advancing a first jaw member towards a second jaw member to grip tissue therebetween prior to driving the fasteners into tissue. The apparatus further includes a registering means on the cartridge utilized with the surgical fastening apparatus of the present invention to permit insertion or loading of a cartridge which is specific for that instrument and the operation for which the instrument is to be used. The registering means prevents loading of a cartridge that is not compatible with the instrument on which it is being mounted. The registering means of the cartridge of the present invention also provides a means for grasping the cartridge to facilitate loading onto the jaw mechanism of the surgical fastening apparatus, and as such provides a visual as well as a tactile indication of the compatibility of the cartridge with the instrument upon which it is being mounted. The registering means of the present invention includes at least one tab member which extends outwardly from the cartridge where the tab member registers with a complementary shaped notch in the jaw member on which the cartridge is mounted. The cartridge preferably provides the tab member at a location which is specific for a particular cartridge, such as a specific number of staples or fasteners, a particular arrangement or orientation of the fasteners, and/or a particular size of the staple or fastener. The tab member is positioned in such a location as to be compatible only with an instrument that will accept those fasteners and the arrangement of the fasteners within the cartridge. Accordingly, incompatible cartridges would not fit on a particular instrument. In addition, the cartridge may include alignment means which assists in aligning the cartridge as it is inserted into the jaw member so that the cartridge is properly aligned with the anvil jaw to form the fasteners or the staples that are disposed therein. The alignment means preferably includes a groove which is positioned on at least one side of the cartridge and is perpendicular to the longitudinal axis of the instrument. A complementary detent is provided on at least one side of the cartridge jaw, which is preferably formed as a pair of jaw arms for accepting the cartridge therebetween.

BRIEF DESCRIPTION OF THE DRAWINGS

The foregoing features of the present invention will become more readily apparent and may be understood by referring to the following detailed description of an illustrative embodiment of the cartridge for use with a surgical fastening device, taken in conjunction with the accompanying drawings, in which.

DETAILED DESCRIPTION OF THE PREFERRED EMBODIMENTS

Figure 1:
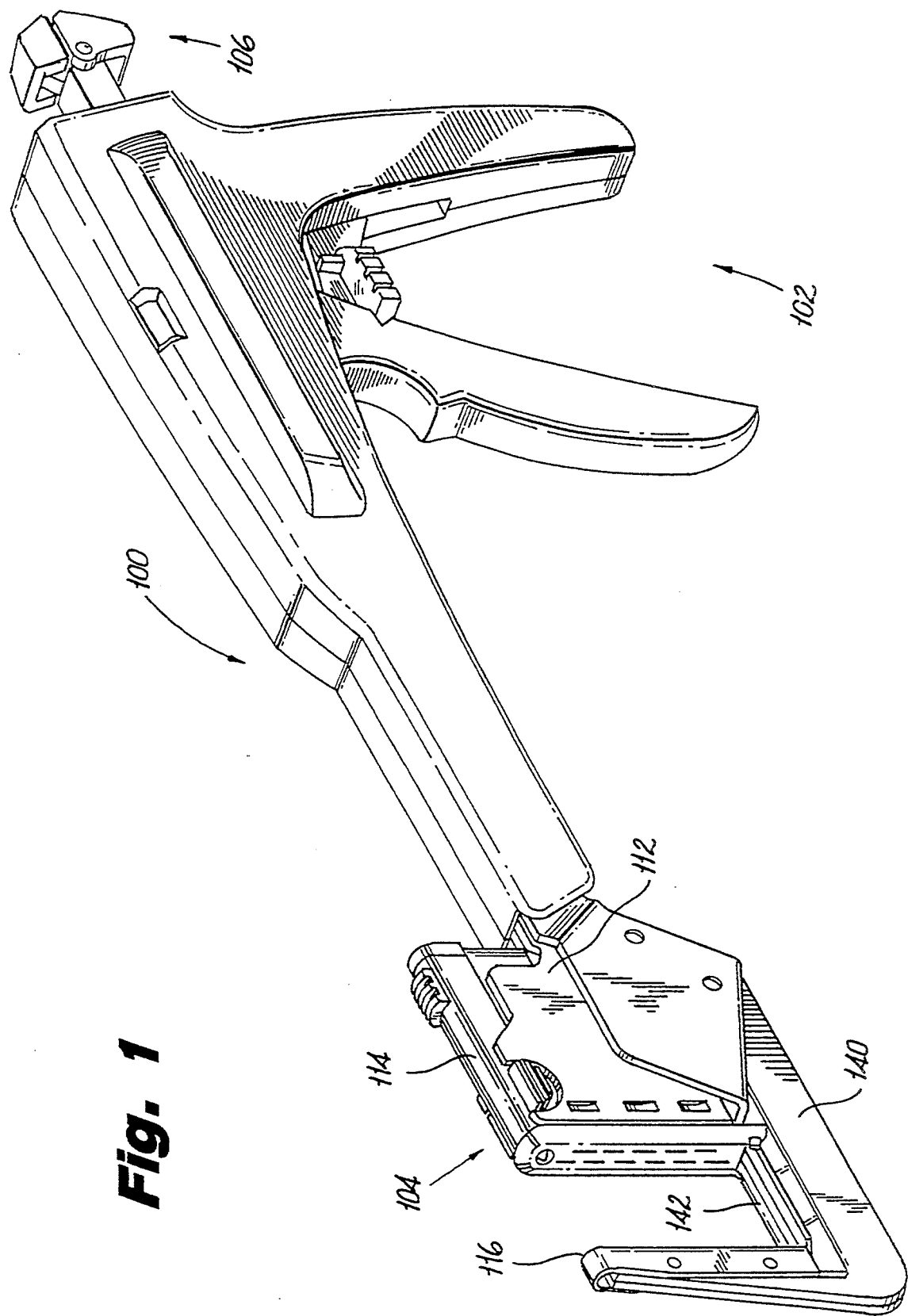
FIG. 1 is a perspective view of the complete surgical fastener applying instrument having a cartridge according to the present invention positioned thereon.

Referring now in specific detail to the drawings, in which like reference numerals identify similar or identical elements throughout the several views, there is shown in FIG. 1 a surgical fastener applying instrument 100 having a cartridge and jaw mechanism according to the present invention. FIG. 1 further illustrates the registering means and alignment means for the cartridge of the present invention. As seen in FIG. 1, a surgical fastener applying instrument 100 includes a handle mechanism 102 and a jaw mechanism 104. An advancing means 106 is provided for approximating the cartridge jaw 112 towards the anvil jaw 116 to position tissue therebetween to effect the stapling or fastening procedure. Positioned on cartridge jaw 112 is a cartridge 114 having the registering means of the present invention, which will be described below. Positioned on U-shaped frame portion 104 is guiding track 142 to receive and cooperate with a guiding means on the cartridge as described below. Positioned on U-shaped frame portion 140 is guiding track 142 to receive and cooperate with a guiding means on the cartridge as described below. Extending from the handle mechanism 102 to the jaw mechanism 104 is a driving mechanism for firing the staples or fasteners in cartridge 114 in response to movement of handle mechanism 102. The mechanisms for advancing the cartridge jaw 112 and for firing the fasteners are not part of the present invention and therefore will not be discussed herein. Details concerning the mechanisms can be found in commonly assigned copending U.S. application Ser. No. 07/779,505, filed Oct. 18, 1991 which is incorporated herein by reference.

Figure 2:
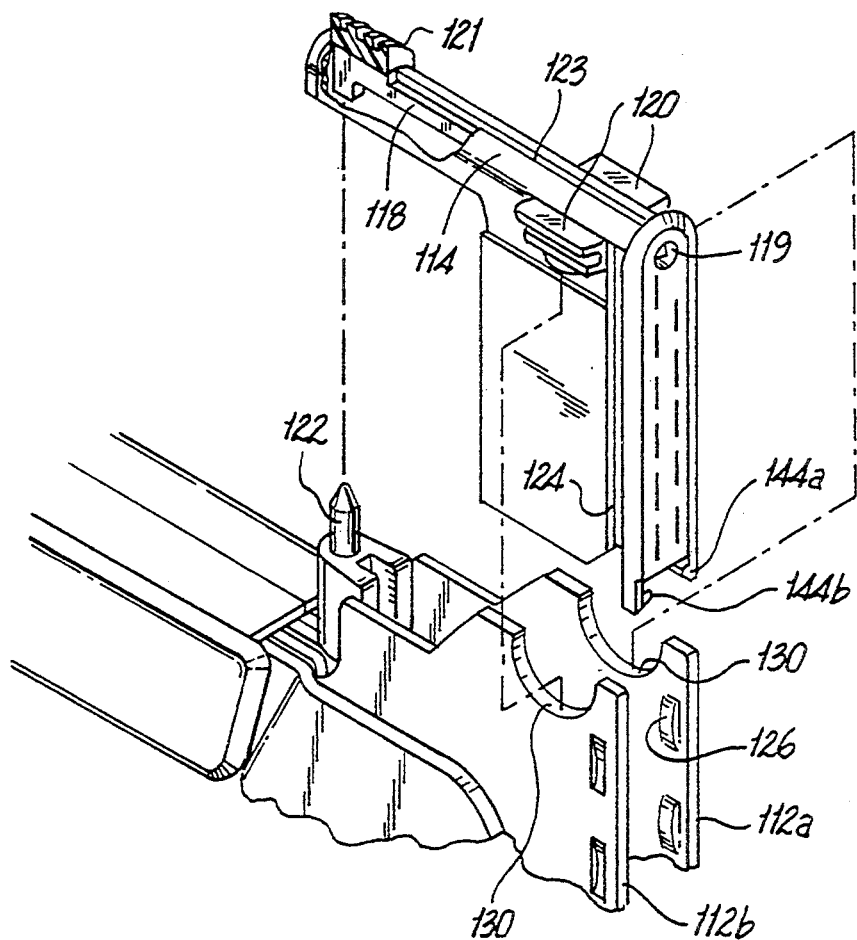
FIG. 2 is an exploded perspective view showing the cartridge and jaw mechanism of the present invention.

As seen in FIG. 2, cartridge 114 is positioned on jaw mechanism 112 by sliding the cartridge between jaw arms 112a and 112b. The cartridge preferably is aligned with the cartridge jaw 112 through the provision of vertical grooves 124 which register with complementary detents 126 which are provided on the cartridge jaw arms 112a and 112b. As cartridge 114 is inserted into cartridge jaw 112, tab members 120 align with and register with complementary notches 130 to form the registering means of the present invention. Tab members 120 may be provided on one or both sides of cartridge 114 as shown in FIG. 2, to ensure loading of a cartridge 114 which is compatible with instrument 100 as predetermined for the particular application. Of course, it is contemplated that the tab member and notch arrangement can be reversed, i.e. the tab positioned on the jaw mechanism and the notch on the cartridge. Cartridge 114 further includes an alignment pin 118 which is engaged by coupling post 122. Pin 118, manually slidable by movement of slide member 121 in slot 123, extends through opening 119 to extend into the anvil jaw 116 to assist in aligning the cartridge and anvil jaw 116. Cartridge 114 also includes guide posts 144a and 144b designed to guide cartridge 114 so that cartridge 114 is aligned with the anvil surface on anvil jaw 116 on U-shaped portion 140 during advancement and firing.

Figure 3:
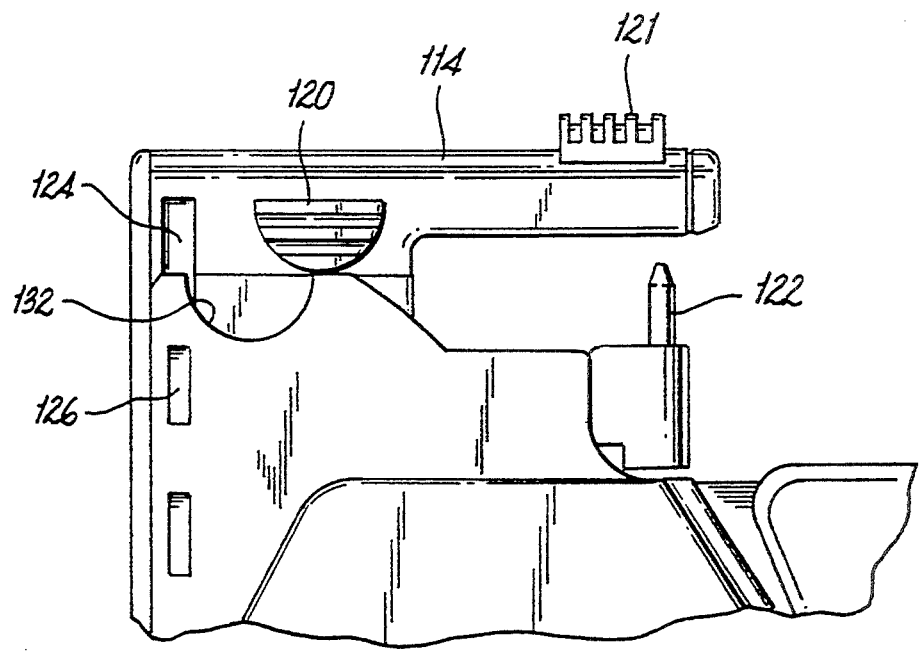
FIG. 3 is a side plan view showing a cartridge having the registering means of the present invention where an incompatible cartridge is partially inserted into the instrument.

As seen in FIG. 3, the provision of tab members 120 prevents the loading of an incompatible cartridge 114 in the jaw mechanism 112. Specifically, tab members 120 would only align and register the cartridge with a compatible jaw mechanism, and will not be properly seated in an incompatible notch 132 as shown. For example, if the instrument is designed to apply two linear rows of fasteners, it will have two linear rows of anvil depressions formed on anvil jaw member 116 for forming the fasteners. Such an instrument will only receive replacement cartridges having two rows of fasteners adapted for alignment with the anvil depressions, as only the tabs of these cartridges will register with the notches in jaw 112. If the user attempts to load a cartridge having three linear rows of fasteners, such as those used in vascular applications, the tabs on the cartridge will not be in alignment with the notches and the cartridge cannot be loaded in the instrument. Similarly, this tab/notch arrangement can be utilized if desired to control the interchangeability of cartridges containing fasteners of different sizes or orientations.

Tab members 120 preferably have a tapered, knurled or stepped surface which facilitates grasping and holding the cartridge as it is loaded onto jaw mechanism 112. It is also contemplated that the surface of tab members 120 provide a tactile indication to the surgeon of the particular cartridge 114 which has been chosen. To this end, it is contemplated that the surface of tab members 120 could include some indication surface such as knurling, stepped grooves, indentations, detents, etc., which would provide a tactile indication of which cartridge has been chosen.

The term "fasteners" is used herein as a generic term which includes surgical staples, and the staple-shaped portion of two-part surgical fasteners, and equivalence thereof. It is further understood that the fasteners described herein are applicable to instruments for applying metal staples, as well as staples and two-pan fasteners made from non-bioabsorbable or from bioabsorbable polymers (e.g. polyglycolide, polylactide and copolymers thereof).

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for applying surgical fasteners, comprising:
   a jaw mechanism including a first jaw member having a cartridge member containing a plurality of fasteners, and a second jaw member;

advancing means for approximating said first jaw member and said second jaw member to position tissue therebetween;

driving means for driving said fasteners from said cartridge member;

registering means for positioning said cartridge member on said first jaw member;

first receiving means disposed on said first jaw member complementary to said registering means for receiving said registering means;

aligning means for positioning said cartridge member with respect to said first jaw member;

second receiving means disposed on said first jaw member complementary to said aligning means for receiving said aligning means;

guiding means disposed on said cartridge member to guide said cartridge member into alignment with an anvil surface on said second jaw member; and means disposed on said second jaw member complementary to said guiding means for receiving said guiding means;

wherein said guiding means comprises at least one inwardly extending tab member on a lower end portion thereof, and said means on said second jaw member comprises at least one track member complementary to said guiding means for receiving said guiding means; and wherein said at least one tab member extends beneath said at least one track member.

2. An apparatus according to claim 1, wherein said registering means comprises at least one tab member on said cartridge member and wherein said first receiving means comprises at least one complementary notch on said first jaw member.

3. An apparatus according to claim 2, wherein said at least one tab member of said registering means includes means for grasping said cartridge member to facilitate removal of said cartridge member from said first jaw member.

4. An apparatus according to claim 1, wherein said aligning means comprises at least one groove on said cartridge member and wherein said second receiving means comprises at least one complementary detent on said first jaw member.

5. An apparatus according to claim 4, wherein said at least one groove is disposed perpendicular to a longitudinal axis of said apparatus.

6. An apparatus according to claim 1, wherein said at least one track member is disposed parallel to a longitudinal axis of said apparatus.

* * * * *